US012426806B2

(12) United States Patent
Suzuki et al.

(10) Patent No.: US 12,426,806 B2
(45) Date of Patent: Sep. 30, 2025

(54) DISPLAY CONTROL METHOD, DISPLAY CONTROL DEVICE AND STORAGE MEDIUM

(71) Applicants: CASIO COMPUTER CO., LTD., Tokyo (JP); ASICS CORPORATION, Kobe (JP)

(72) Inventors: Shosaku Suzuki, Machida (JP); Takeshi Yokoi, Tokyo (JP); Ken Kusano, Hyogo (JP); Noriko Nishimura, Hyogo (JP); Masaru Ichikawa, Hyogo (JP); Takehiro Tagawa, Hyogo (JP)

(73) Assignees: CASIO COMPUTER CO., LTD., Tokyo (JP); ASICS CORPORATION, Hyogo (JP)

( * ) Notice: Subject to any disclaimer, the term of this patent is extended or adjusted under 35 U.S.C. 154(b) by 472 days.

(21) Appl. No.: 17/949,810

(22) Filed: Sep. 21, 2022

(65) Prior Publication Data
US 2023/0098294 A1    Mar. 30, 2023

(30) Foreign Application Priority Data
Sep. 30, 2021 (JP) .................................. 2021-160622

(51) Int. Cl.
*A61B 5/11* (2006.01)
*A61B 5/00* (2006.01)

(52) U.S. Cl.
CPC ........... *A61B 5/1118* (2013.01); *A61B 5/1123* (2013.01); *A61B 5/743* (2013.01)

(58) Field of Classification Search
CPC .......... A61B 5/11; A61B 5/112; A61B 5/7445
See application file for complete search history.

(56) References Cited

U.S. PATENT DOCUMENTS 9,700,242 B2    7/2017  Utsunomiya et al.
2007/0275830 A1*  11/2007  Lee ...................... A61B 5/1038
                                                          482/54
(Continued)

FOREIGN PATENT DOCUMENTS

JP    2012179114 A    9/2012
JP    2014138661 A    7/2014
(Continued)

OTHER PUBLICATIONS

Japanese Office Action (and an English language translation thereof) dated Aug. 15, 2023, issued in counterpart Japanese Application No. 2021-160622.

*Primary Examiner* — Mark A Connolly
(74) *Attorney, Agent, or Firm* — Holtz, Holtz & Volek PC

(57) ABSTRACT

Provided is a display control method for a display control device including a processor and a storage. The method includes generating first display data for a display to display user marks at intervals so as to be added one by one as a time elapses from a timing. The intervals each correspond to a user's step length of a user obtained based on measured data on running or walking of the user. The user marks each represent a position where a foot of the user lands by one step. The method further includes generating second display data for the display to display reference marks at intervals so as to be added one by one as the time elapses. The intervals each correspond to a predetermined reference step length. The reference marks each represent a position where a reference foot lands by one step.

15 Claims, 10 Drawing Sheets

(56) References Cited

U.S. PATENT DOCUMENTS

2015/0325004 A1 11/2015 Utsunomiya et al.
2015/0325270 A1 11/2015 Utsunomiya et al.
2017/0360333 A1* 12/2017 Shideler ................ A61B 5/742

FOREIGN PATENT DOCUMENTS

| | | | |
|---|---|---|---|
| JP | 2015042241 A | 3/2015 | |
| JP | 2015084868 A | 5/2015 | |
| WO | WO-0139130 A1 * | 5/2001 | ............. G06T 15/50 |
| WO | 2008120477 A1 | 10/2008 | |
| WO | 2014112632 A1 | 7/2014 | |
| WO | WO-2016061667 A1 * | 4/2016 | ............. A61B 5/112 |

* cited by examiner

DISPLAY CONTROL METHOD, DISPLAY CONTROL DEVICE AND STORAGE MEDIUM

CROSS-REFERENCE TO RELATED APPLICATIONS

This application is based upon and claims the benefit of priority from Japanese Patent Application No. 2021-160622 filed on Sep. 30, 2021, the entire content of which is incorporated herein by reference.

BACKGROUND

Technical Field

The present disclosure relates to a display control method, a display control device and a storage medium.

Description of Related Art

There is a technology for portable devices to measure the state of walking, running or the like. There has been a larger number of portable devices not only counting the number of steps but also providing more detailed information. In JP 2012-179114 A, there is disclosed a technique of measuring a time during which both feet are in contact with the ground in order to evaluate deterioration in a walking function.

SUMMARY

A display control method is a display control method for a display control device including a processor and a storage being performed by the processor executing a program stored in the storage, the display control method including:
  (i) generating first display data for a display to display user marks at intervals each corresponding to a user's step length of a user obtained based on measured data on running or walking of the user so as to be added one by one as a time elapses from a timing, the user marks each representing a position where a foot of the user lands by one step; and
  (ii) generating second display data for the display to display reference marks at intervals each corresponding to a predetermined reference step length so as to be added one by one as the time elapses, the reference marks each representing a position where a reference foot lands by one step.

BRIEF DESCRIPTION OF SEVERAL VIEWS OF DRAWING

The accompanying drawings, which are incorporated in and constitute a part of the specification, illustrate embodiments, and together with the general description given above and the detailed description of the embodiments given below, serve to explain the principles of the present disclosure, wherein.

DETAILED DESCRIPTION

Hereinafter, one or more embodiments of the present disclosure will be described with reference to the drawings.

Figure 1:
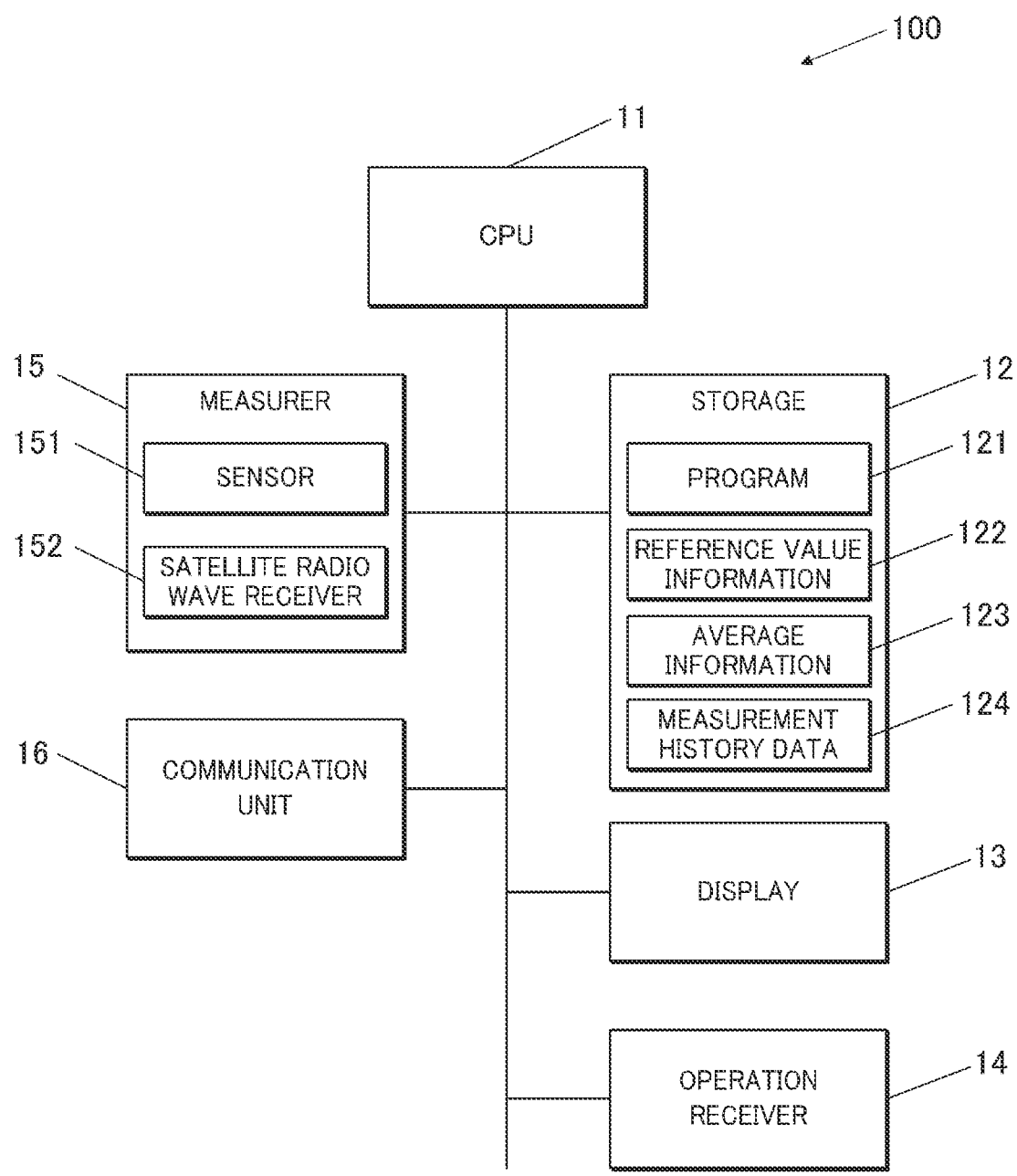
FIG. 1 is a block diagram showing a functional configuration of an electronic device including a display control device of an embodiment(s)

FIG. 1 is a block diagram showing a functional configuration of an electronic device 100 including a display control device of an embodiment(s).

The electronic device 100 is, for example, a portable device, such as a smartphone. The electronic device 100 includes a central processing unit (CPU) 11, a storage 12, a display 13, an operation receiver 14, a measurer 15 and a communication unit 16. The CPU 11 and the storage 12 constitute the display control device.

The CPU 11 is a hardware processor that performs arithmetic processing and overall control of operation of the electronic device 100. There may be one CPU 11 or two or more CPUs 11 that perform parallel processing or distributed processing for a purpose. The CPU 11 may have a logic circuit or the like dedicated to specific processing.

The storage 12 includes a volatile memory (RAM; Random Access Memory) and a nonvolatile memory. The volatile memory provides the CPU 11 with a memory space for working and stores temporary data. The nonvolatile memory is, for example, a flash memory, and stores programs 121, setting data, obtained data and so forth.

The programs 121 are for processes that the CPU 11 reads and executes. The programs 121 include a control program to control overall operation of the electronic device 100 and various application programs. The application programs include a running/walking management program described below. The setting data stored in the nonvolatile memory of the storage 12 includes reference value information 122 and average information 123, and the obtained data stored therein includes measurement history data 124. These will be described later.

The display 13 has a display screen and, under the control of the CPU 11, displays letters, marks, figures, graphs and so forth on(in) the display screen. The display screen is not limited to but a liquid crystal display (LCD).

The operation receiver 14 receives operations from a user and generates operation-received signals, and outputs the operation-received signals to the CPU 11. The operation receiver 14 has, for example, a touchscreen overlaid on the display screen. In addition to this, the operation receiver 14 may have push-button switches, slide switches and so forth.

The measurer 15 includes a sensor 151 and a satellite radio wave receiver 152 for obtaining physical quantities on running or walking. In the present disclosure, the "running or walking (running/walking)" means not an exclusive choice of one of running and walking but at least one of these, and these two may not be treated distinctively in measurement and analysis. Examples of the sensor 151 include an acceleration sensor. Although not particularly limited, the acceleration sensor measures acceleration in three axes that are orthogonal to one another. While a person is running/walking, characteristic change occurs cyclically in acceleration in the vertical direction, the change corresponding to foot landing on the ground, kicking and so forth. Further, while a person is running/walking, change occurs cyclically in acceleration in the right-left direction perpendicular to the direction of travel/movement, the change corresponding to the right-left motion of the body that corresponds to the right foot and the left foot alternately leaving the ground. Still further, change occurs cyclically in acceleration in the direction of travel/movement each time a person kicks the ground with his/her foot. By identifying these on the basis of measured data by the acceleration sensor (sensor 151), the CPU 11 can identify each step (foot landing/leaving or foot contact/off) of the user in running/walking, and count the number of steps of the user.

The satellite radio wave receiver 152 includes an antenna and a circuit, and receives radio waves from positioning satellites and decodes and demodulates the radio waves to obtain necessary signals. The signals, which are obtained from the positioning satellites, each include orbital information on a positioning satellite and current date-and-time information. The CPU 11 performs positioning calculation to identify the current position of the electronic device 100 on the basis of difference between the current positions and the current points of time (current date and time) of the (four or more) positioning satellites of the timing at which the satellite radio wave receiver 152 receives radio waves from the positioning satellites. By identifying change in the current position of the electronic device 100 at intervals of a unit time, the CPU 11 can obtain moving speed, namely, running/walking speed, of the user.

The communication unit 16 includes an antenna and a circuit, and controls transmission and reception of data to and from external devices in accordance with a communication standard. The communication standard is not particularly limited to, but, for example, a communication standard for short-range wireless communication, such as Bluetooth®, or a communication standard for a wireless LAN. The communication unit 16 may obtain (receive) measured data on running/walking from an external device. In this case, the external device is, for example, a measurement device that is used in a state of being fixed to a part of the body, such as an arm, torso or a leg, with a belt, a band or the like wrapped around the part, or a measurement device that is used by in a state of being put in a pocket or the like. In the case of a measurement device that contacts the human body, the measurement device may be capable of measuring a pulse rate (heart rate) and oxygen saturation ($SpO_2$) in addition to those on running/walking.

The electronic device 100 may further include, as an informing unit that informs the user of various pieces of information, a motor that generates vibrations or beeps, a speaker that outputs sound, and an LED that lights up or blinks in a certain color (or multiple colors).

Next, recording, management and display control of running/walking motion by the running/walking management program included in the programs 121 of this embodiment will be described.

The electronic device 100 of this embodiment measures data on running/walking of the user with the measurer 15, and/or obtains measured data on running/walking of the user from an external device that the user uses, in particular, a measurement device that is put on the body of the user, and displays the running/walking state of the user based on the measured data.

Figure 2:
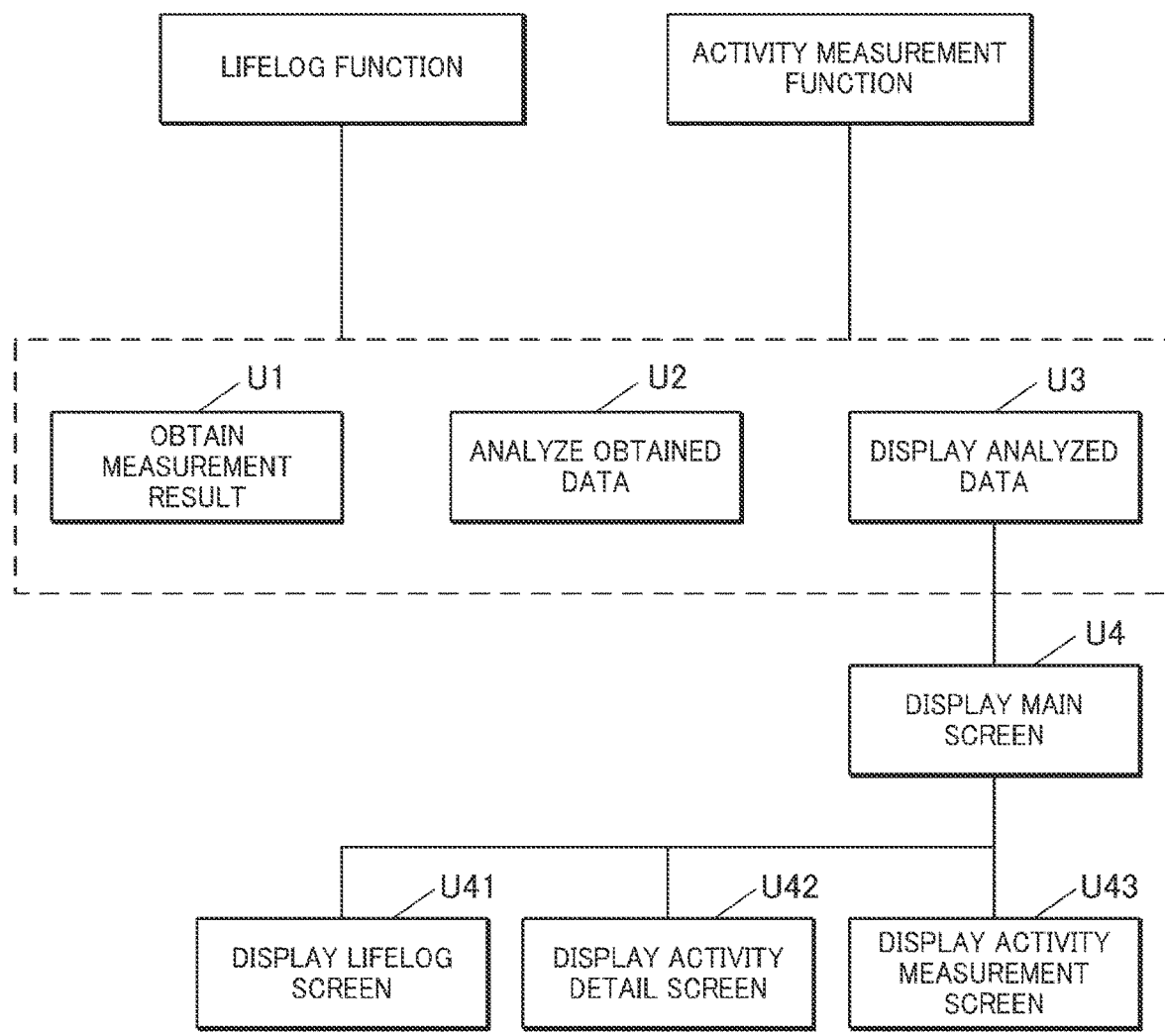
FIG. 2 is an illustration to explain what is managed by a running/walking management program.

FIG. 2 is an illustration to explain what is managed by the running/walking management program.

The running/walking management program of this embodiment has two types of functions, a lifelog function and an activity measurement function.

The lifelog function is a function that continuously obtains, for example, data on all running/walking in daily life as long as the measurer 15 operates or measurement results are obtainable from an external device. The activity measurement function is a function that is executed/started by a user operation when he/she is going to take exercise (intentional motion), thereby obtaining data on running/walking of the user, who is assumed to be taking exercise. Even while the activity measurement function is running, the lifelog function keeps running in parallel with the activity measurement function.

In either of the functions, measurement results (measured data) are obtained (U1), and an analysis process of running/walking based on the obtained measured data is performed (U2). The analysis process includes identifying the number of steps in running/walking (the number of steps, i.e., the number of times that a foot lands on or leaves from the ground in running/walking). The analysis process further includes calculating calories burned and so forth on the basis of the identified number of steps and information on the sex, age (date of birth), weight and so forth set by the user making input operations on the operation receiver 14, for example. If available, measured data of a pulse rate and oxygen saturation may be obtained.

In addition to these, at least while the activity measurement function is running, distance covered, stride (step length) and moving speed by/of running/walking of the user are obtained.

These analysis results (analyzed data) are displayed on the display screen of the display 13 (U3). The display contents are switchable between a summary displayed in the main screen (U4), histories of results obtained by the lifelog function by the day before (U41), details of an activity measurement that has finished (U42), and a real-time activity measurement that is currently being performed (U43).

Figure 3:
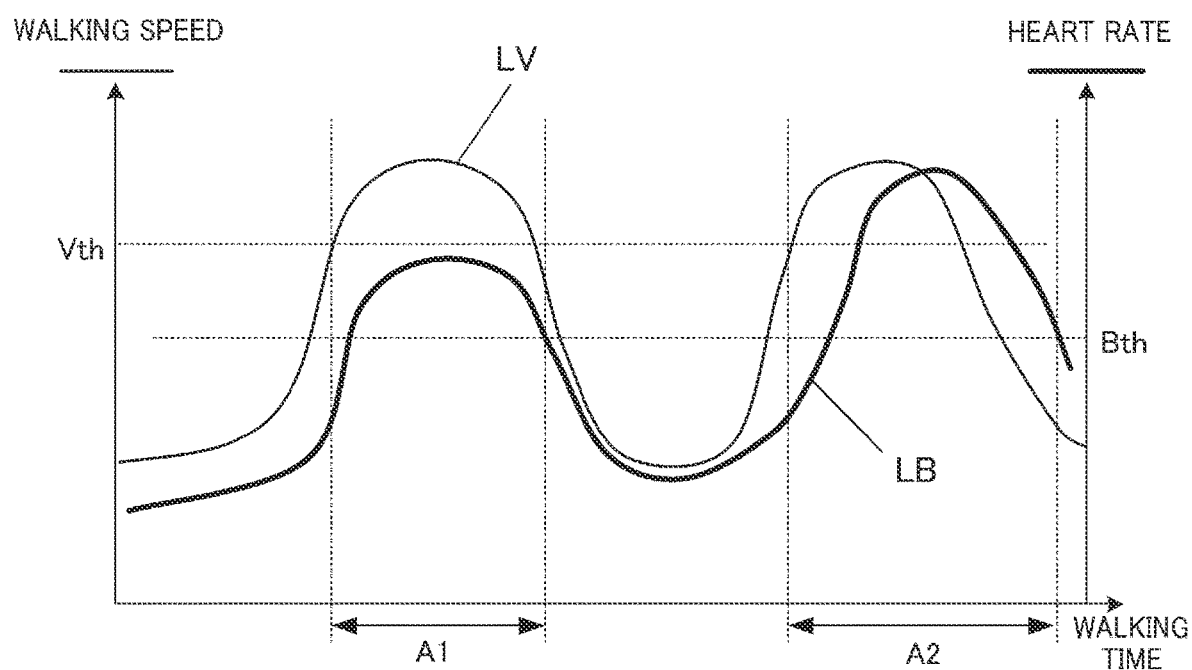
FIG. 3 is an illustration to explain change in walking speed and change in heart rate during execution of an activity measurement function (activity measurement)

FIG. 3 is an illustration to explain change in walking speed and change in heart rate during execution of the activity measurement function. When the user starts the activity measurement function, he/she may not start an activity immediately, or may have a break (which includes an unplanned stop due to a traffic light or the like). The activity may be interval training (interval walk or interval run), in which running/walking motion at a target speed and running/walking motion at a speed slower than the target speed are alternately performed. Interval training is an effective activity (intentional motion, exercise, training, etc.). In this embodiment, an activity is walking.

During execution of the activity measurement function, whether it is an active walk or not is determined on the basis of a reference value Vth for walking speed and a reference value Bth for heart rate (pulse rate). If the walking speed LV is equal to or greater than the reference value Vth, or if the heart rate LB is equal to or greater than the reference value Bth, it is determined that an active walk (fast walk) is being performed. In this embodiment, periods A1, A2 in FIG. 3 are active walk (fast walk) periods. The average walking speed of the active walk indicates, for example, the magnitude of exercise load, and the average heart rate during the active walk indicates the physical strength/fitness level of the user against the exercise load. Periods other than the active walk periods are referred to as normal walk periods, which include break/stop time.

In the case where the electronic device 100 is a smartphone or the like that can detect and measure the acceleration or the like but not the heart rate (pulse rate), whether it is an active walk or not may be determined on the basis of the walking speed only.

The reference value Vth shown in FIG. 3 differs according to the sex and the age of the user. In general, the older the user is, the lower his/her physical strength level is. Hence, the reference value Vth may be lower as the user is order. The reference values Vth for respective sexes and ages (generations) are stored as the reference value information 122, which is setting data. They may be stored by being installed together with the running/walking management program. The reference value Vth for the user may be determined by taking another parameter(s), such as the height thereof, into account.

Figure 4:
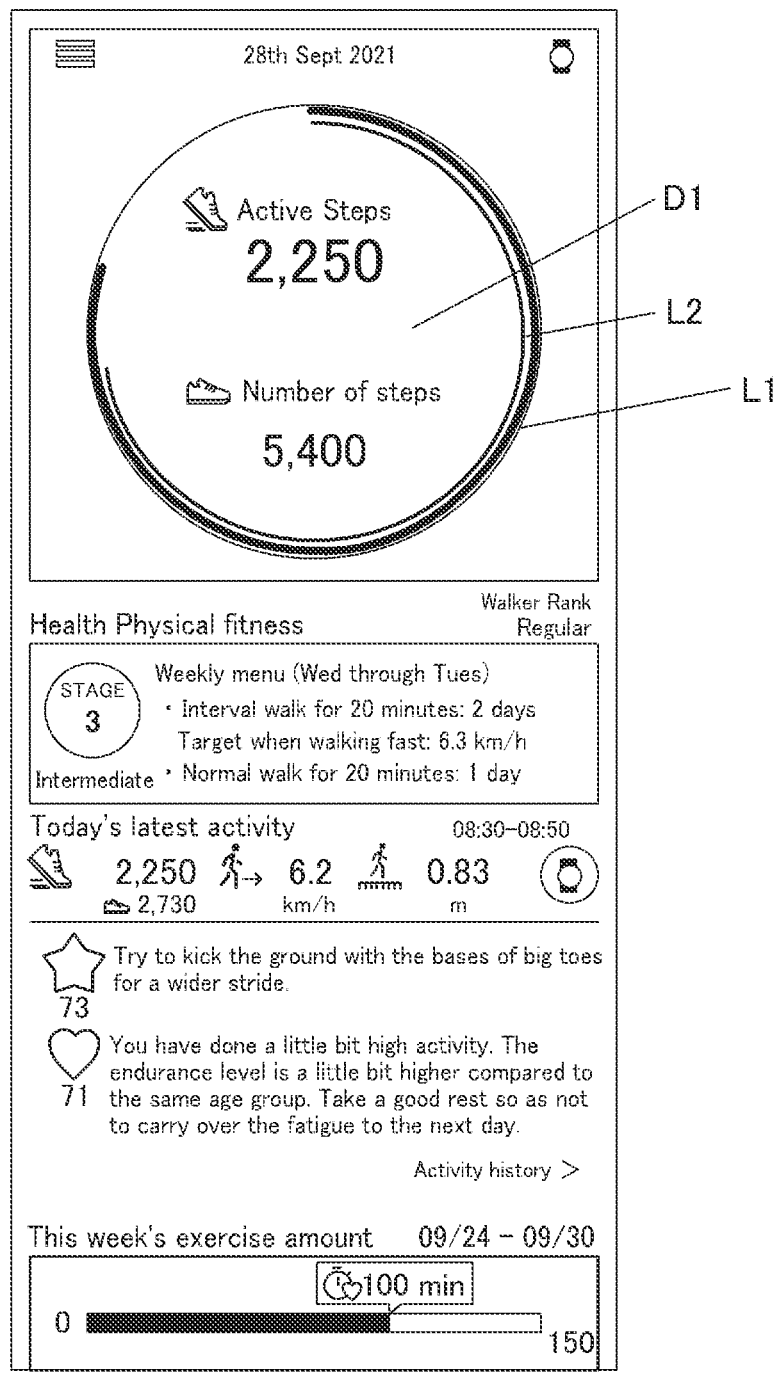
FIG. 4 shows an example of the main screen displayable at the time of and during execution of the running/walking management program.

FIG. 4 shows an example of the main screen (display window) displayable at the time of and during execution of the running/walking management program.

The screen shown in each of FIG. 4 to FIG. 7 does not show all the actual display objects, and also does not necessarily show its actual screen size. That is, contents actually displayed in each screen of the electronic device 100 may include objects other than those shown in each of FIG. 4 to FIG. 7, or in practice, scrolling may be needed to display all the contents shown in each of FIG. 4 to FIG. 7.

In this main screen, the total number of steps on a day obtained by the lifelog function and the number of steps of the active walk (number of active steps) on the day identified during execution of the activity measurement function are displayed together in a circle D1 (U4 in FIG. 2). This allows the user to easily know how much the user walks in his/her daily life and how much of it is done by an activity(ies). In this embodiment, a thick line L1 and a thin line L2 along the circumference of the circle D1 show, in real time, degrees of achievement to targets set for the number of active steps (exercise amount) that is obtained by the activity measurement function and the total number of steps that is obtained by the lifelog function, respectively.

In the main screen, in addition to the abovementioned numbers of steps, contents of an exercise program set by the user as a target activity, a summary of results (main results) of the latest activity measurement, scores (evaluation values) and so forth are displayed. Exercise programs may be set any time by the user making input operations on the operation receiver 14. At the time, the electronic device 100 may suggest/propose duration, speed and so forth on the basis of, for example, the measurement history so far (e.g., the measurement history data 124) in order to make the exercise load be an appropriate magnitude.

The electronic device 100 may give a rank and/or set a stage to encourage the user to continue exercising on the basis of his/her exercise continuation history, physical strength level and so forth.

Figure 5:
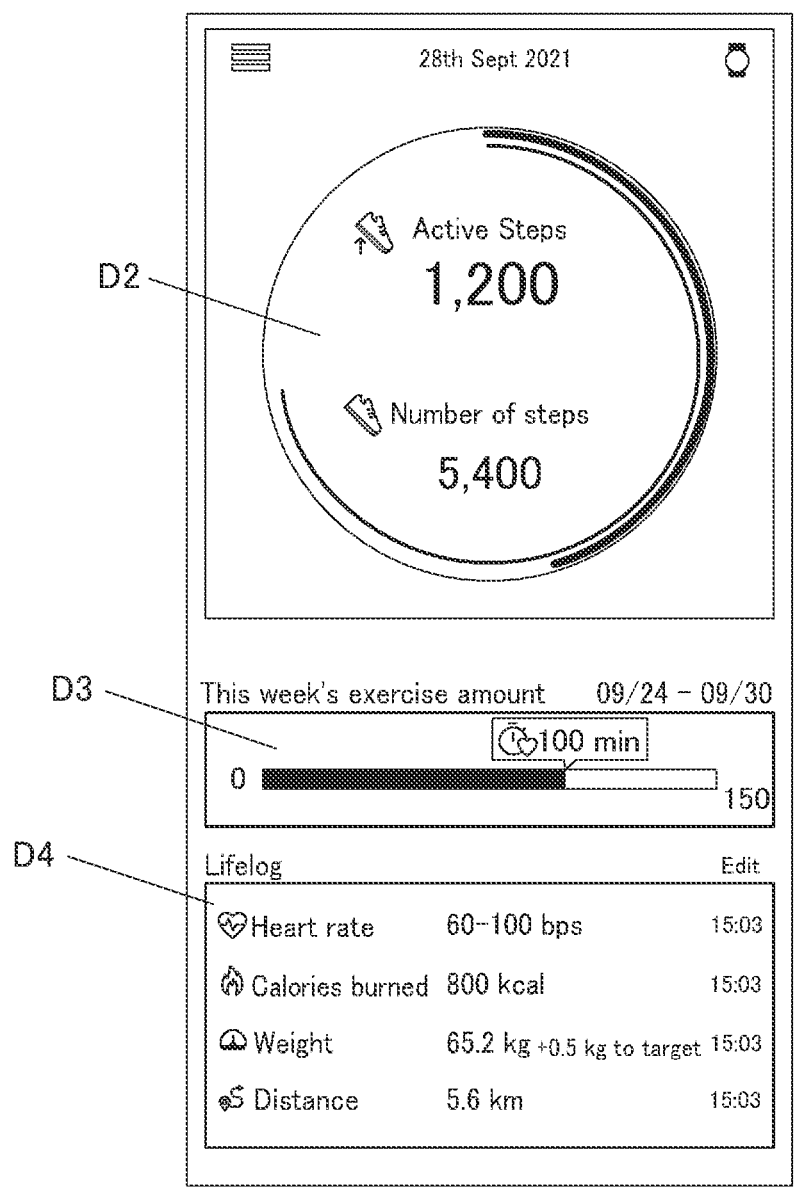
FIG. 5 shows an example of a lifelog screen.

FIG. 5 shows an example of a lifelog screen (display window).

In this screen too, as in the main screen, the total number of steps on a day and the number of active steps on the day are displayed together in a circle D2 (U41 in FIG. 2). In a display section D3 for "This week's exercise amount", the active-walk-performed time so far in the latest (current) week (100 minutes in FIG. 5) is displayed to the target time of the week (150 minutes in FIG. 5). The start of a week does not need to be Sunday or Monday. The first day of a week may be automatically determined on the basis of the day of a week on which an exercise program is set, or may be set in response to an input operation made by the user. In a lifelog section D4 at the lower part of the screen, the recent state of each parameter is displayed. As described above, about the weight or the like, an input value that is input by the user and received by the operation receiver 14 is used.

When the CPU 11 detects an operation (e.g., a tap) for selecting one of the portion where the numbers of steps are displayed (D2), the portion where the exercise amount is displayed (D3), the respective rows of the heart rate, calories burned, weight and distance (D4), the history of the parameter concerned (selected) may be displayed. The history may be displayed, for example, weekly, monthly or yearly in a switchable manner. The displayable history data of these is kept in the storage 12 as the measurement history data 124 for an appropriate period of time. The measurement history data 124 may be stored not locally in the electronic device 100, but in an external data server, such as a cloud server, to be managed thereby in a state of being able to be referenced at any time.

Figure 6A:
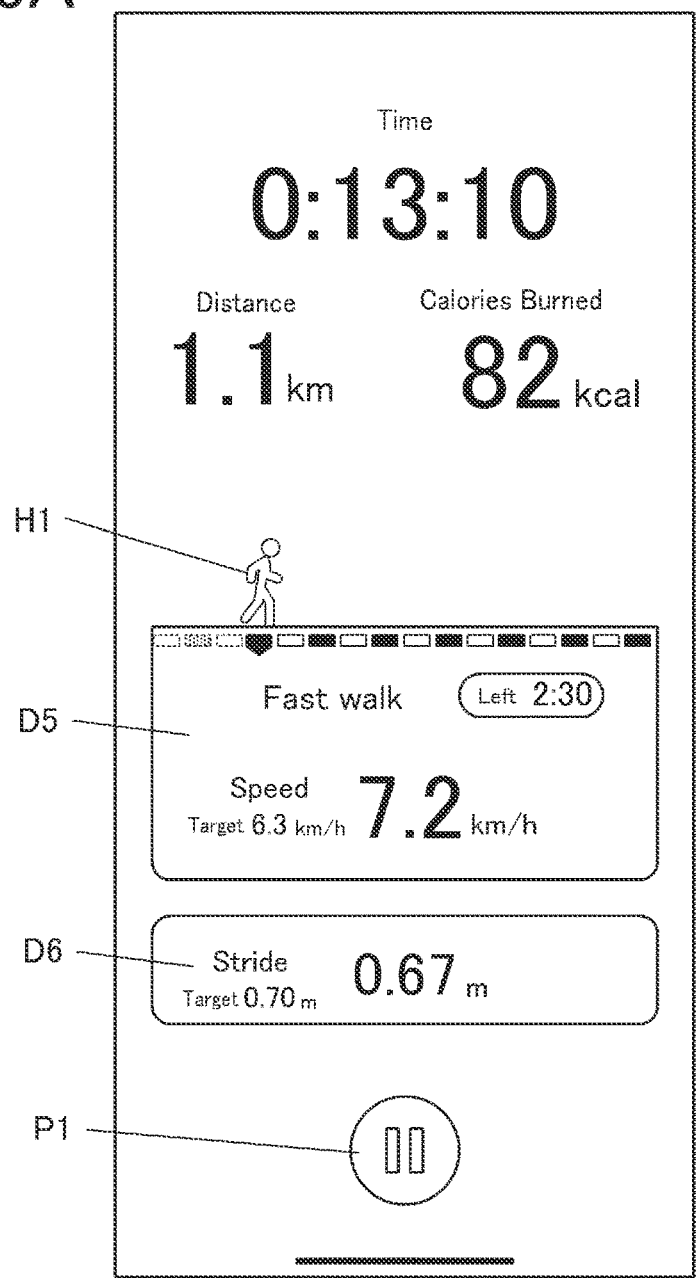
FIG. 6A shows an example of a screen displayable during activity measurement.
Figure 6B:
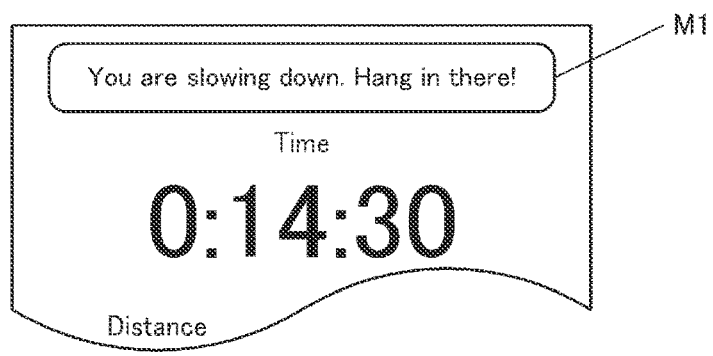
FIG. 6B shows another example of the screen displayable during activity measurement.

FIG. 6A and FIG. 6B show two examples of a screen (display window) displayable during activity measurement, namely, during execution of the activity measurement function.

This screen is displayable from the time at which an activity measurement execution command is obtained (received by the operation receiver 14) until the time at which an activity measurement end command is obtained (U43 in FIG. 2).

Activity measurement is stopped by an operation on a stop button P1 displayed at the lower part of the screen shown in FIG. 6A as an example. While activity measurement stops (which includes when activity measurement is just started), a start button for starting/restarting activity measurement is displayed in place of the stop button P1.

FIG. 6A shows the screen displayable during interval walk.

At the upper part of the screen, elapsed time from the start of the interval walk, distance covered and calories burned so far are displayed. At the center part of the screen, a display section D5 and a display section D6 are located. In the display section D5, an average value of moving speed (walking speed) of the active walk (fast walk) in a period of the interval walk is displayed. In the display section D6, an average value of stride is displayed. These values are calculated in real time and displayed together with their target values. If the real-time average values are below their respective target values, the display mode of the real-time average values, such as color, is changed (e.g., to red) for the user to easily recognize the fact. Further, as shown in FIG. 6B, which shows another example of the screen, a message M1 may be displayed in a pop-up manner above the elapsed time displayed. Further, by taking into account that users does not look at the display screen so often during activities, the electronic device 100 may be configured to inform the user of the fact that his/her average value(s) is below the target value(s) not only by display but also by sound, vibrations or the like. Further, not only when the user's average value(s) is below the target value(s), but also when the user's average value(s) exceeds the target value(s) too much, the electronic device 100 may inform the user of the fact in the same/similar manner.

In interval walk, an active walk for a predetermined period of time and a walk (inactive walk) slower than the active walk for a predetermined period of time are alternately performed. In the display section D5, the progress of the walking state and the remaining time in the current state are displayed. In FIG. 6A, along the upper side of the display section D5, solid black rectangles representing the active walk and black-framed rectangles representing the inactive walk are alternately displayed, and rectangles corresponding to the finished periods have been replaced by those with low contrast against the background, and the current period is represented by a pentagon with a downward protrusion, which has replaced a rectangle. The current period may be displayed in a blinking mode or the like. Further, just above the display section D5, i.e., on the upper side of the display section D5, an animation or the like of a walking person figure H1 is displayed at a position in the right-left direction corresponding to the current period.

Thus, the electronic device 100 performs, during an activity, various types of output, which includes display, for the user to easily know the progress of the activity and the degrees of achievement to the targets.

Figure 7:
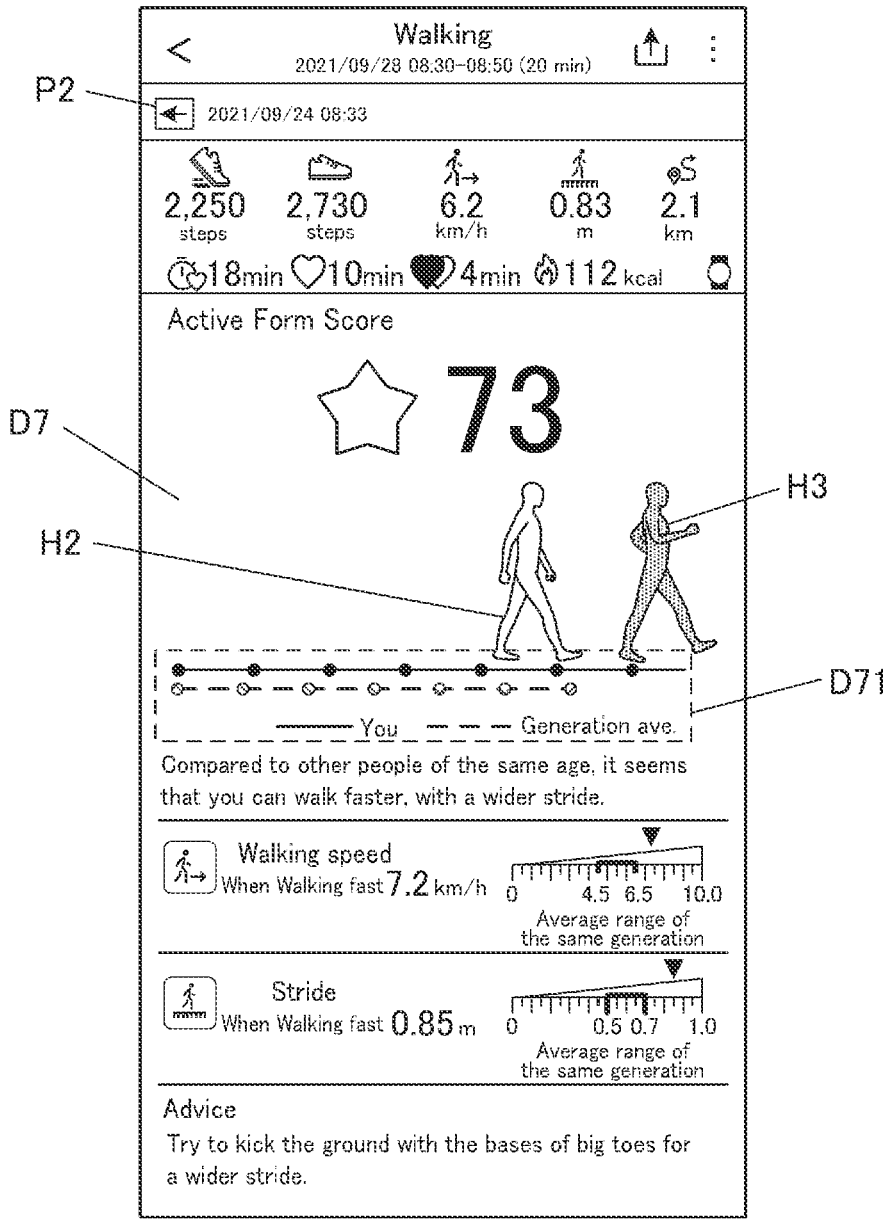
FIG. 7 shows an example of a screen where results of execution of an activity (results of activity measurement) are displayed.

FIG. 7 shows an example of a screen (display window) where results of execution of an activity (results of activity measurement) are displayed.

In this screen, results of execution of an activity that has finished are displayed in detail, the results including analysis results and evaluations (evaluation values) (U42 in FIG. 2).

In FIG. 7, at the upper part of the screen, as the results of execution of a selected activity (selected activity measurement), the numbers of steps, average speed, stride, duration, distance covered, calories burned and so forth are displayed.

In a display section D7 thereunder, an active form score is displayed as an evaluation value based on the calculated walking speed (user's moving speed) and stride (user's step length) of the user. The active form score is an example of a parameter that expresses comparison of these with the average walking speed (reference moving speed) and stride (reference step length) of the same generation as the user. As the walking speed and the stride of the user are faster and longer than those of the same generation, respectively, the active form score is higher. In FIG. 7, together with the calculation results of the walking speed and the stride of the user, their average ranges of the same generation are displayed. The average ranges are, for example, each a range of an average value of samples ±1σ obtained from measured/calculated data of sampled other users of the same generation as the user. The average ranges for respective sexes and ages (generations) are stored/kept as the average information 123 (shown in FIG. 1).

The average information 123, which is setting data, may be installed together with the reference value information 122 and the running/walking management program, to be obtained, written and stored/kept in the storage 12. If a cloud server or the like as a provider of the running/walking management program performs unified management of measurement history data of many users, average values and their variations may be recalculated on the basis of the measurement history data, which is stored in the provider, at appropriate intervals by a management program or the like of an agent or the like that manages the provider, and the recalculation results may be transmitted to the electronic device 100 to update the average information 123.

In a sub-section D71 in the display section D7, in which the active form score is displayed, the calculated stride and moving speed are compared and displayed with the average values of the same generation as the user (hereinafter "generation average(s)"). This comparative display is performed not by still display but animation display. For example, the amount of movement (movement amount) based on the moving speed of the generation average (comparison target) is represented by a broken line (second line). The broken line is extended (lengthened) as time elapses from a position on the left side on the screen to the right side thereon (in a direction). That is, the length of the broken line indicates the movement amount (reference movement amount). Then, marks (shaded circles, reference marks) representing respective steps, namely, respective positions at each of which a reference foot lands (foot landing positions), are displayed on the broken line (so as to correspond to the broken line) at intervals each corresponding to a reference stride so as to be added in order (one by one) as the broken line extends (time elapses), which reproduces movement/travel of the generation average in a period of a predetermined number of steps (e.g., six steps), namely, up to the foot landing of the last step of a predetermined number of steps (e.g., foot landing of the sixth step). At the time, an animation of a person figure H2 representing a reference person who moves by running/walking is displayed, and moves parallel to the broken line as the head position of the broken line moves.

In order to be easily compared with this comparison target, the amount of movement of the user (user's movement amount) based on the calculated moving speed of the user is represented by a solid line (first line). The broken line and the solid line are displayed with the same position on the left side on the screen in the right-left direction (direction in which the first line and the second line extend) as a starting point. The solid line is extended (lengthened) as the time elapses from the position (starting point) on the left side on the screen to the right side thereon (i.e., parallel with the broken line) from the same timing (a timing) as that of the broken line. Then, marks (black circles, user marks) representing respective positions at each of which a foot of the user lands (foot landing positions) are displayed on the solid line (so as to correspond to the solid line) at intervals each corresponding to a user's stride so as to be added in order (one by one) as the solid line extends (time elapses), which reproduces movement/travel of the user in the abovementioned period. At the time, an animation of a person figure H3 representing the user who moves by running/walking is displayed, and moves parallel to the solid line, namely, in FIG. 7, moves on the same line as the person figure H2, which represents the generation average, as the head position of the solid line moves.

The extension of the lines (solid line and broken line) and the animations of the person figures H2, H3 may be automatically repeated. The number of frames of the animations may be determined as appropriate according to the load of the electronic device 100 and viewability of the animations.

Figure 8A:
FIG. 8A is an illustration to explain how animations on walking move forward, wherein the timing is the initial timing.
Figure 8B:
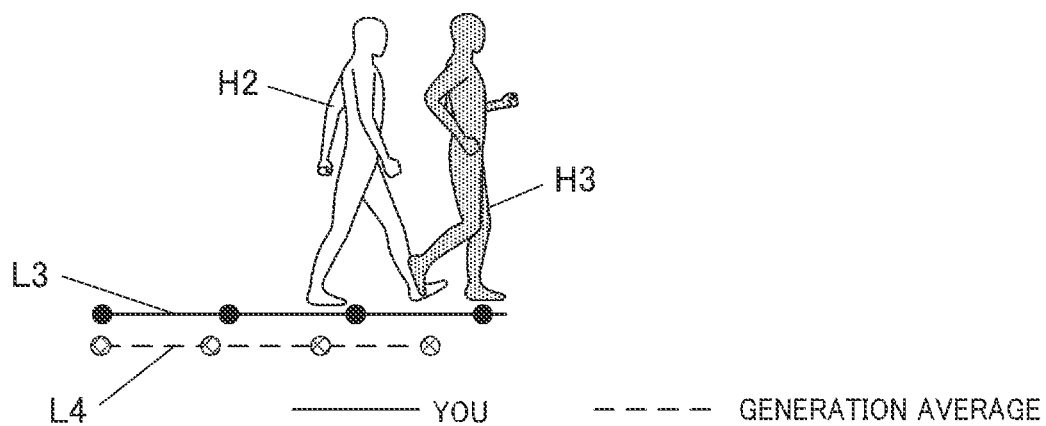
FIG. 8B is an illustration to explain how the animations on walking move forward, wherein the timing is later than the initial timing.
Figure 8C:
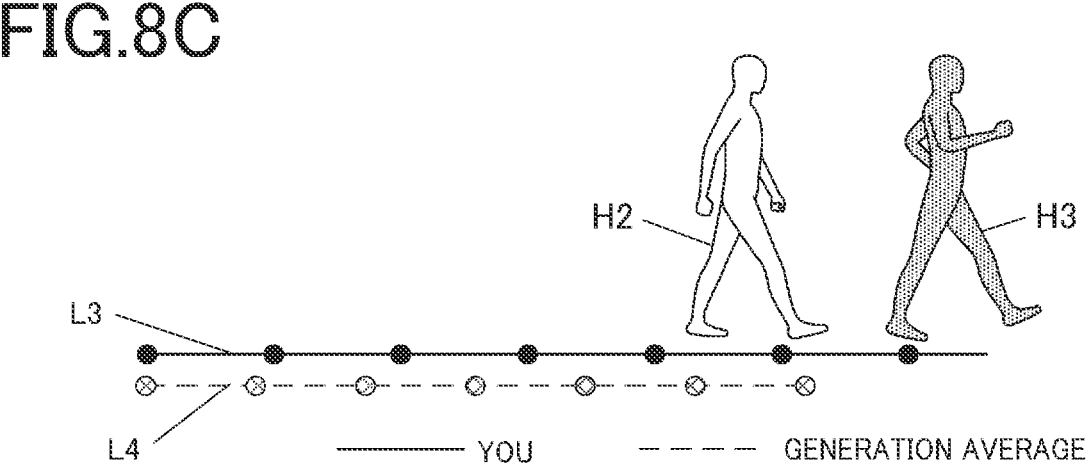
FIG. 8C is an illustration to explain how the animations on walking move forward, wherein the timing is later than the timing of FIG. 8B.

FIG. 8A to FIG. 8C are illustrations to explain how the animations on walking move forward.

FIG. 8A shows the person figures H2, H3 at the foot landing timing of the first step(s) (initial timing). FIG. 8B shows the person figures H2, H3 at a timing later than the initial timing. FIG. 8C shows the person figures H2, H3 at a timing later than the timing of FIG. 8B. Thus, the longer the elapsed time from the initial timing is, the more the person figures H2, H3 move rightward, and accordingly the more a solid line L3 representing the person figure H3 and a broken line L4 representing the person figure H2 extend rightward. Further, regarding each of the person figures H2, H3, circles each representing a foot landing position by one step are added one by one. The rightward movement of the person figure H3 and the rightward extension of the solid line L3 are faster than the rightward movement of the person figure H2 and the rightward extension of the broken line L4, and also the space/distance between the person figure H3 that moves ahead and the person figure H2 that moves behind becomes wider/longer. This allows the user to intuitively know that his/her moving speed is faster than the generation average, which is the comparison target. Also, spatial intervals and temporal intervals at which circles each representing a foot landing position of the user appear are wider and shorter than those at which circles each representing a foot landing position of the generation average appear, respectively. This allows the user intuitively know that his/her stride (distance per one step, i.e., step length) is longer than the generation average, and his/her pitch (time per one step, i.e., step time) is shorter than the generation average.

The moving speed (reproduction speed) of the animations may be a predetermined coefficient (e.g., "2") times faster (fast-forward) or slower than the actual time passing speed (normal speed).

The values, such as the active form score shown in the display section D7 in FIG. 7, may be a standard deviation (deviation value) from the mean value (average value) or may be a value corresponding thereto. The average level in this case is not limited to 50, but may be adjusted as appropriate. Alternatively, relative levels may be adjusted as appropriate such that the active form score or the like is expressed, for example, in terms of 100 points being a perfect score.

Figure 9:
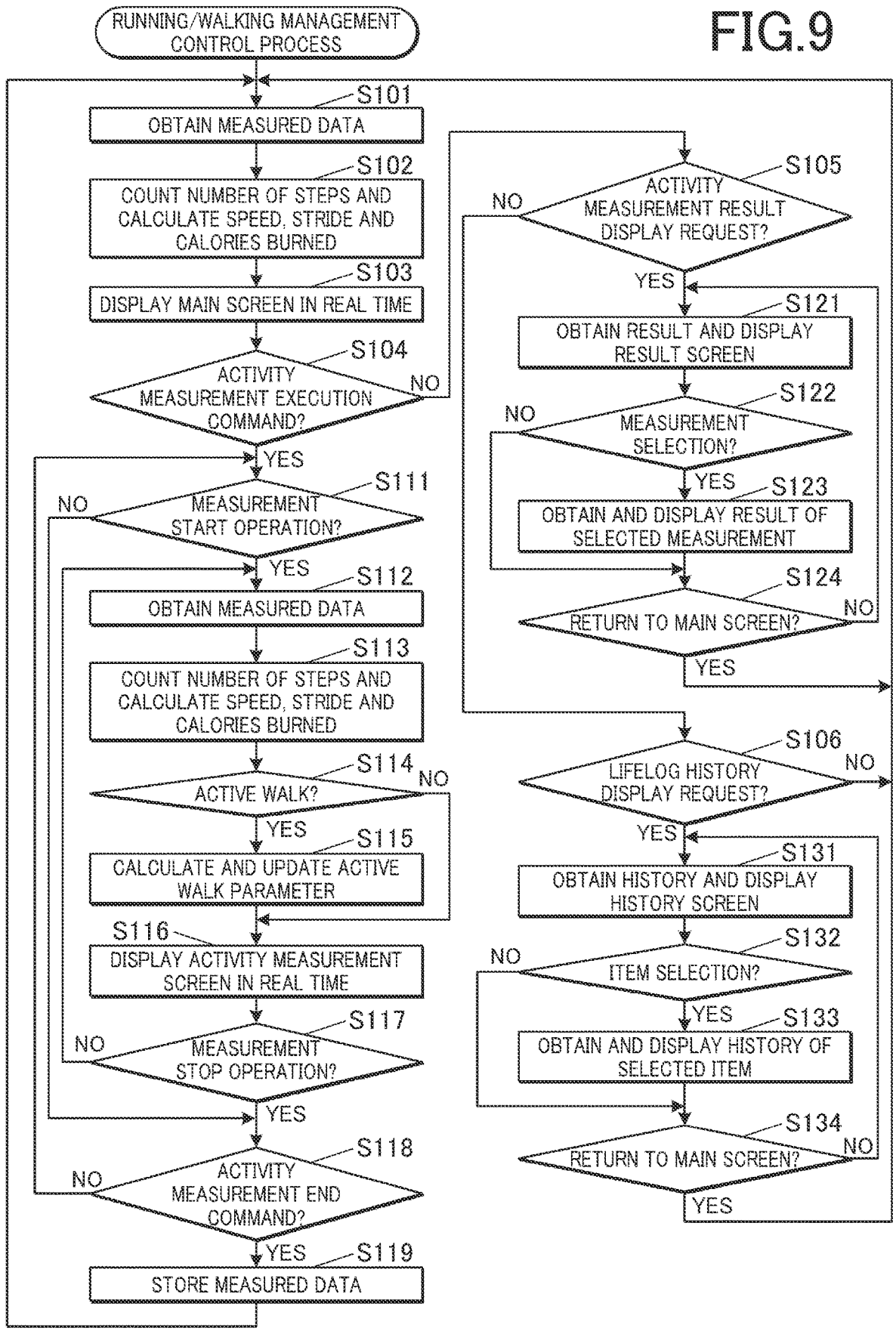
FIG. 9 is a flowchart showing a control procedure of a running/walking management control process.

FIG. 9 is a flowchart showing a control procedure that is taken by the CPU 11 in a running/walking management control process included in the running/walking management program. This process is started when the running/walking management program is selected and started, and continuously performed until it is ended by an interrupt process or the like. Various setting processes or the like irrelevant to the contents of the present disclosure are excluded here and their descriptions will be omitted.

When the running/walking management control process is started, the CPU 11 first performs initial settings of: securing a memory capacity; obtaining setting data; starting the components of the measurer 15 and/or securing communication connection with an external device having a sensor(s) if they are not performed yet; performing settings for starting display windows; and so forth, and then obtains measured data from the measurer 15 and/or the external device (Step S101, U1 in FIG. 2). On the basis of the obtained measured data, the CPU 11 counts the number of steps of the user and also calculates the walking speed, stride and calories burned of the user (Step S102, U2 in FIG. 2). The CPU 11 causes the display 13 to display the counted and calculated contents (e.g., numerical values) in the main screen in real time (Step S103, U3 in FIG. 2). The contents displayed in the main screen (e.g., shown in FIG. 4) in Step 103 include not only the number of steps related to the lifelog function but also the number of active steps as described above.

The CPU 11 determines whether it has obtained an activity measurement execution command (Step S104). If the CPU 11 determines that it has obtained an activity measurement execution command (Step S104; YES), the CPU 11 determines whether the operation receiver 14 has received a measurement start operation (Step S111). If the CPU 11 determines that the operation receiver 14 has not received a measurement start operation (Step S111; NO), the CPU 11 proceeds to Step S118.

If the CPU 11 determines that the operation receiver 14 has received a measurement start operation (Step S111; YES), the CPU 11 obtains measured data (Step S112). On the basis of the obtained measured data, the CPU 11 counts the number of steps and also calculates the speed, stride and calories burned (Step S113).

On the basis of the calculated speed and a heart rate if obtained, the CPU 11 determines whether an active walk condition(s), which is described above, is satisfied (Step S114). If the CPU determines that the active walk condition is satisfied (Step S114; YES), the CPU 11 calculates and updates active walk parameters (average value of speed, average value of stride, duration, etc.) (Step S115). Then, the CPU 11 proceeds to Step S116. If the CPU 11 determines that the active walk condition is not satisfied (Step S114; NO), the CPU 11 proceeds to Step S116.

In Step S116, the CPU 11, in real time, updates (display contents in) an activity measurement screen (e.g., shown in FIG. 6A and FIG. 6B) and causes the display 13 to display the activity measurement screen (Step S116). At the time, the CPU 11 may cause the display 13 to additionally display a pop-up message or the like suitable for the obtained latest values of the parameters or the like. The display contents therein may include not only numerical values related to the active walk but also the total number of steps obtained by the lifelog function.

The CPU 11 determines whether the operation receiver 14 has received a measurement stop operation (Step S117). If the CPU 11 determines that the operation receiver 14 has not received a measurement stop operation (Step S117; NO), the CPU 11 returns to Step S112. If the CPU 11 determines that the operation receiver 14 has received a measurement stop operation (Step S117; YES), the CPU 11 determines whether it has obtained an activity measurement end command (Step S118). If the CPU 11 determines that it has not obtained an activity measurement end command (Step S118; NO), the CPU 11 returns to Step S111.

If the CPU 11 determines that it has obtained an activity measurement end command (Step S118; YES), the CPU 11 obtains evaluations, which are described above, on the basis of the measured, counted and calculated values obtained by the activity measurement, and adds/stores the measured, counted and calculated values and the evaluations to/in the measurement history data 124 of the storage 12 together with date-and-time data and so forth (Step S119). Then, the CPU 11 returns to Step S101.

In Step S104, if the CPU 11 determines that it has not obtained an activity measurement execution command (Step S104; NO), the CPU 11 determines whether the operation receiver 14 has received an input operation for an activity measurement result display request (Step S105). If the CPU 11 determines that the operation receiver 14 has received an input operation for an activity measurement result display request (Step S105; YES), the CPU 11 obtains results of the latest activity measurement and causes the display 13 to display a result screen (e.g., shown in FIG. 7) to display the obtained results therein (Step S121).

The CPU 11 determines whether any measurement in the past has been selected, for example, by the user using a left arrow P2 shown in FIG. 7 (Step S122). If the CPU 11 determines that a measurement in the past has been selected (Step S122; YES), the CPU 11 obtains data of results of the selected measurement and causes the display 13 to display a result screen, which is, if not the same, similar to that shown in FIG. 7, to display the obtained data therein (Step S123). Then, the CPU 11 proceeds to Step S124. In Step S122, if the CPU 11 determines that no measurement in the past has been selected (Step S122; NO), the CPU 11 proceeds to Step S124.

In Step S124, the CPU 11 determines whether it has obtained a main screen return request (i.e., whether the operation receiver 14 has received an input operation for the request) (Step S124). At the time, the CPU 11 may be obtaining measured data related to the lifelog function as appropriate, and also may be performing the analysis process as needed, which includes counting the number of steps, by background processing.

If the CPU 11 determines that it has obtained a main screen return request (Step S124; YES), the CPU 11 returns to Step S101. If the CPU 11 determines that it has not obtained a main screen return request (Step S124; NO), the CPU 11 returns to Step S121.

In Step S105, if the CPU 11 determines that the operation receiver 14 has not received an input operation for an activity measurement result display request (Step S105; NO), the CPU 11 determines whether it has obtained a lifelog history display request (i.e., whether the operation receiver 14 has received an input operation for the request) (Step S106). If the CPU 11 determines that it has not obtained a lifelog history display request (Step S106; NO), the CPU 11 returns to Step S101.

If the CPU 11 determines that it has obtained a lifelog history display request (Step S106; YES), the CPU 11 obtains history data related to the lifelog function and causes the display 13 to display a history screen (e.g., shown in FIG. 5) (Step S131). The CPU 11 determines whether the operation receiver 14 has received an input operation for selecting an item from items displayed in the history screen (Step S132). If the CPU 11 determines that the operation receiver 14 has received an input operation for selecting an item (Step S132; YES), the CPU 11 obtains history data of the selected item and causes the display 13 to display the history data in chronological order (Step S133). Then, the CPU 11 proceeds to Step S134. If the CPU 11 determines that the operation receiver 14 has not received an input operation for selecting an item (Step S132; NO), the CPU 11 proceeds to Step S134.

In Step S134, the CPU 11 determines whether the operation receiver 14 has received an input operation for a main screen return request (i.e., whether it has obtained a main screen return request) (Step S134). At the time, the CPU 11 may be obtaining measured data related to the lifelog function as appropriate, and also may be performing the analysis process as needed, by background processing. If the CPU 11 determines that the operation receiver 14 has received an input operation for a main screen return request (Step S134; YES), the CPU 11 returns to Step S101. If the CPU 11 determines that the operation receiver 14 has not received an input operation for a main screen return request (Step S134; NO), the CPU 11 returns to Step S131.

Figure 10:
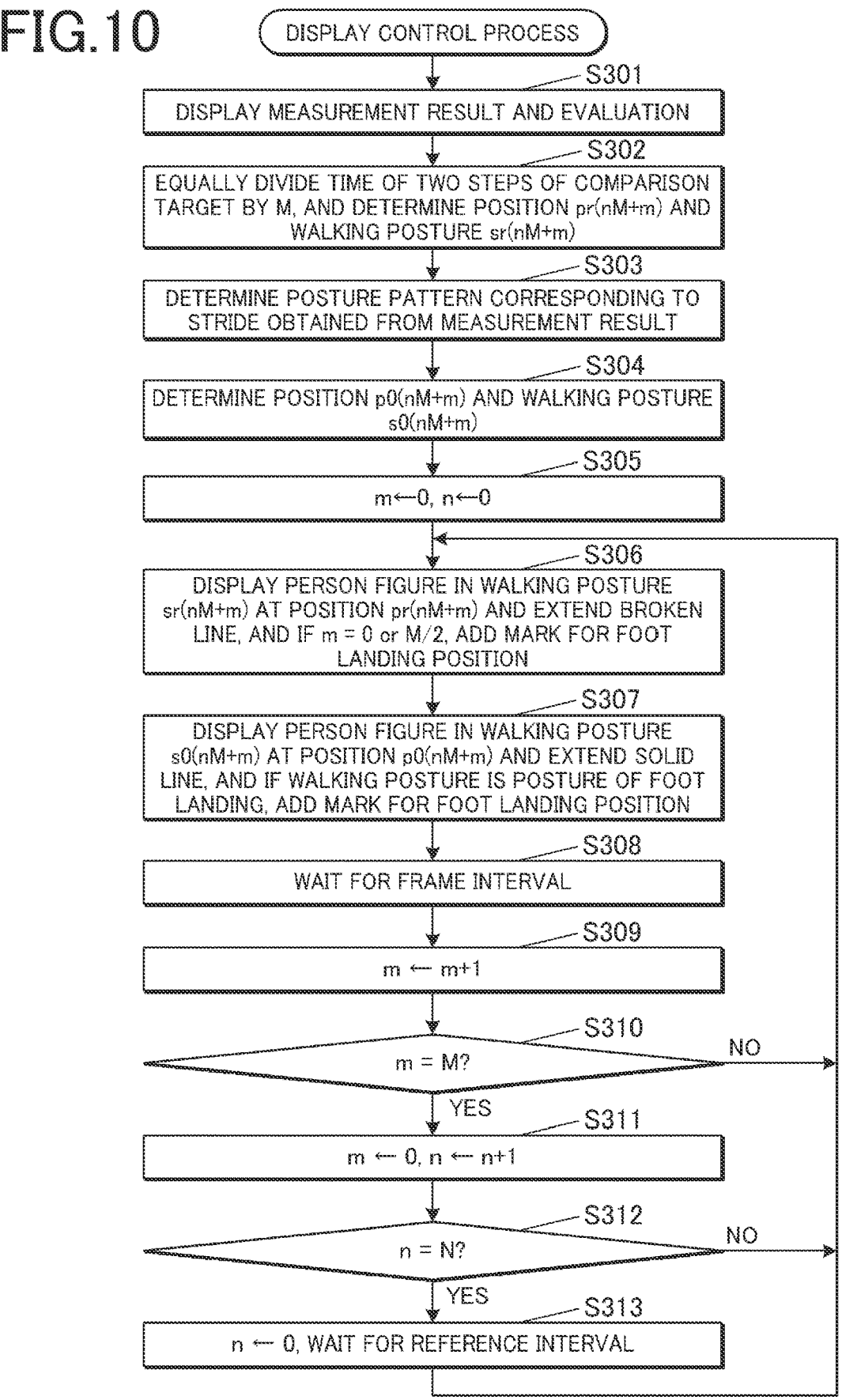
FIG. 10 is a flowchart showing a control procedure of a display control process to display results of activity measurement.

FIG. 10 is a flowchart showing a control procedure that is taken by the CPU 11 in a display control process related to the display process in each of Steps S121, S123, in which results of activity measurement are displayed. The display control process is started each time the display contents are updated/replaced with the next/previous ones, and keeps being performed until the undated/replaced display contents are updated/replaced with the next/previous ones again.

When the display control process is started, the CPU 11 causes the display 13 to perform still display of measurement results, analysis results (counting results, calculation results) based on the measurement results, evaluations thereof and/or the like (i.e., to display the contents so as not to change once they are displayed) (Step S301). Then, the CPU 11 equally divides a time of two steps (one step by the left leg and one step by the right leg) of the comparison target by a predetermined number of partitions (i.e., divisor) M (e.g., 8) to obtain a unit time, and determines a position pr(nM+m) and a walking posture sr(nM+m) thereat (Step S302). The position pr(nM+m) represents a position corresponding to a movement amount from the initial position each time the unit time elapses from the initial timing in a period of the number of cycles N (movement by 2×N steps). The "n" and "m" represent variables (integers, $0 \leq m < M$), and the "nM+m", "n×M+m" to be exact, represents the number of lapses of the unit time from the initial timing. That is, the position pr((nM+m) and the walking posture sr(rnM+m) respectively represent the position and the walking posture at the timing when the unit time elapses (nM+m) times, namely, "n×M+m" times, from the initial timing. The divisor M is the number of types of changing posture that can be recognized by users with their eyes as a continuous image (moving image) when images with the types of changing posture are displayed at intervals. The person figure H2 is displayed with its position being changed, by images with the posture of types, the number of which is equal to the divisor M, being displayed at frame intervals in order a plurality of times that is equal to the number of cycles N. Image data of a person figure in M types of posture is stored/kept in the storage 12 in advance, and read from the storage 12 and displayed. Alternatively, in the display control process, the CPU 11 may newly generate such image data and display an animation(s) using the generated image data. If the same comparison target is displayed regardless of the generation/age or the sex of the user, the process in Step S302 may be performed in advance so that the data is stored/kept in advance.

The CPU 11 determines a posture pattern, such as the degree of opening of legs, corresponding to the stride obtained from (based on) the measurement results (Step S303). On the basis of the walking speed and the stride obtained from (based on) the measurement results (in this embodiment, on the basis of these compared with the walking speed and the stride of the comparison target), the CPU 11 determines a position p0(nM+m) and a walking posture s0(nM+m) thereat (Step S304). The position p0(nM+m) represents a position corresponding to a movement amount from the initial position at each timing in the period of the number of cycles N.

The CPU 11 sets the variables m and n to 0 (Step S305). The CPU 11 causes the display 13 to display the person figure H2 in the walking posture sr(nM+m) at a position on the display screen (result screen) corresponding to the position pr(nM+m) and accordingly extend the displayed broken line to a position corresponding to the position pr(nM+m), and if the variable m is 0 or M/2, causes the display 13 to put a circle, which represents a foot landing position, on the position on the broken line (the head position of the extended broken line). At the start of Step S306, if the person figures H2, H3 in their previous walking postures sr, s0 are displayed at positions corresponding to their previous positions pr, p0, the CPU 11 deletes these first.

The CPU 11 causes the display 13 to display the person figure H3 in the walking posture s0(nM+m) at a position on the display screen (result screen) corresponding to the position p0(nM+m) and accordingly extend the displayed solid line to a position corresponding to the position p0(nM+m), and if the displayed walking posture s0(nM+m) is the posture of foot landing, the CPU 11 causes the display 13 to put a circle, which represents a foot landing position, on the position on the solid line (the head position of the extended solid line). The CPU 11 waits for a time corresponding to a frame interval of the animations (Step S308).

The CPU 11 adds 1 to the variable m (Step S309). The CPU 11 determines whether the value of the variable m is equal to the divisor M (Step S310). If the CPU 11 determines that the value of the variable m is not equal to the divisor M (Step S310; NO), the CPU 11 returns to Step S306. If the CPU 11 determines that the value of the variable m is equal to the divisor M (Step S310; YES), the CPU 11 sets the variable m to 0, and adds 1 to the variable n (Step S311). The CPU 11 determines whether the value of the variable n is equal to the number of cycles N (Step S312). If the CPU 11 determines that the value of the variable n is not equal to the number of cycles N (Step S312; NO), the CPU 11 returns to Step S306. If the CPU 11 determines that the value of the variable n is equal to the number of cycles N (Step S312; YES), the CPU 11 sets the variable n to 0, and waits for a reference interval (Step S313). Then, the CPU 11 returns to Step S306.

If the walking/running state of a user is measured and managed using, for example, a measurement device disclosed in JP 2012-179114 A, and information thereon increases and numerical values thereof are simply enumerated, it is hard for the user to intuitively know how much difference there is in the walking/running state between the user and a reference.

As described above, the display control method of this embodiment includes generating first display data for the display 13 to display user marks (circles) at intervals each corresponding to a user's step length of a user obtained based on measured data on running or walking of the user so as to be added one by one as time elapses from a timing (initial timing), the user marks each representing a position where a foot of the user lands by one step, and causing the display 13 to display the first display data (Step S307 in FIG. 10), and generating second display data for the display 13 to display reference marks (circles) at intervals each corresponding to a predetermined reference step length so as to be added one by one as the time elapses, the reference marks each representing a position where a reference foot lands by one step, and causing the display 13 to display the second display data (Step S306 in FIG. 10).

Displaying these marks (circles), which represent the foot landing positions of the user and the comparison target, such that rows of the marks extend as the time elapses allows the user to, by looking at these, more intuitively know how much difference there is in the running/walking state between the user and the comparison target (reference values).

The display control method further includes causing the display 13 to display a user's movement amount based on a user's moving speed from the initial timing, the user's moving speed being obtained based on the measured data, using a length of a first line (solid line) that extends in a direction (horizontal/right-left direction of the display screen) as the time elapses from the initial timing (Step S307 in FIG. 10), causing the display 13 to display a reference movement amount based on a reference moving speed (e.g., average moving speed of the same generation/age with the same sex as the user) predetermined as the comparison target from the initial timing using a length of a second line (broken line) that extends in the direction as the time elapses from the initial timing (Step S306 in FIG. 10), and causing the display 13 to display the user marks (circles) and the reference marks (circles), which represent foot landing positions, so as to correspond to the first line and the second line, which are relevant to running/walking, respectively (Steps S306, S307 in FIG. 10).

Displaying the user's movement amount using a (straight) line in animation display according to the elapsed time and the foot landing positions of the user using user marks (circles) parallel to those of the comparison target allows the user to, by looking at these, more intuitively know how much difference there is in the running/walking state between the user and the comparison target (reference values).

In the display control method, it is preferable to cause the display 13 to display the user marks (black circles) on the first line and the reference marks (shaded circles) on the second line as the time elapses. Displaying the foot landing positions of the user and those of the comparison target on the respective lines allows the user to, by simply following the line(s), easily recognize his/her stride (and pitch) with his/her eyes. Further, because it is unnecessary to secure much space either above or under the lines, the lines and the marks can be displayed in a space-saving manner.

The display control method further includes causing the display 13 to display the first line and the second line parallel to one another with the same position in the direction (horizontal/right-left direction of the display screen), in which the first line and the second line extend as the time elapses, as a starting point of the first line and the second line, and causing the display 13 to display, parallel to the first line and the second line, an animation representing the user who moves by running or walking with the user's step length and an animation representing a reference person who moves by running or walking with the reference step length. Displaying the animations that move in the same direction allows the user to easily and clearly recognize, with his/her eyes, difference in the moving speed and difference in the stride between the user and the comparison target, without increasing the display load much.

In the display control method, it is preferable to cause the display 13 to display, on the same line, the animation representing the user at the user's moving speed with the user's step length and the animation representing the reference person at the reference moving speed with the reference step length. Displaying the animations in an overlapping manner allows the user to more directly compare his/her speed and stride with those of the comparison target. That is, it is highly user friendly.

The electronic device 100 includes the display control device of this embodiment. The display control device includes, as a processor, the CPU 11 that obtains measured data on running or walking of a user, generates first display data for the display 13 to display user marks (circles) at intervals each corresponding to a user's step length of the user obtained based on the measured data so as to be added one by one as time elapses from a timing (initial timing), the user marks each representing a position where a foot of the user lands by one step, and causes the display 13 to display the first display data (Step S307 in FIG. 10), and generates second display data for the display 13 to display reference marks (circles) at intervals each corresponding to a predetermined reference step length so as to be added one by one as the time elapses, the reference marks each representing a position where a reference foot lands by one step, and causes the display 13 to display the second display data (Step S306 in FIG. 10). The display control device allows the user to more intuitively know how much difference there is in the running/walking state between the user and the comparison target (reference values), without increasing the display load much.

Further, the running/walking management program 121 including the running/walking management control process of the display control method may be installed in a computer (an information processing system that includes components corresponding to the CPU 11 and the storage 12 of the electronic device 100 and performs display control) to display results of activity measurement. This can provide a simpler way to enable a general-purpose portable device or the like to measure, analyze and display the running/walking state of the user and allows the user to intuitively know the state.

The present disclosure is not limited to the above embodiment(s), but can be modified in various respects.

For example, in the above embodiment, when the animations of the user and the comparison target (generation average) are displayed at their respective walking speeds with their respective strides, the movements of the user and the comparison target are displayed in an overlapping manner, but may be displayed in a partially or completely shifting manner, namely, in a no-overlapping manner, in the vertical direction, for example. Alternatively, their movements may even be displayed three-dimensionally if the electronic device 100 is provided with high display performance. Conversely, if the electronic device 100 is provided with low display performance, the walking state of the comparison target may be displayed, instead of the animation, intermittently at predetermined intervals, for example, by a still image of one or more types being displayed at every two steps, in order to reduce the load. Alternatively, the walking states of the user and the comparison target may not be displayed at all.

Further, in the above embodiment, the comparison target is the generation average, but may be determined by taking not only the age of the user but also another factor, such as the height thereof, into account. Further, instead of the generation average, user's position in the generation from the top expressed by percent, user's past value, target value, ideal value and/or the like may be displayed and used as the comparison target. The comparison target may be switchable between these.

Further, the foot landing positions do not need to be represented by circular marks. For example, they may be represented by marks of another shape, or may be displayed in different colors for the data of the user and the data of the comparison target. Further, the foot landing positions do not need to be represented by the circular marks or the like located on the lines indicating the movement amounts. For example, they may be represented by arrows, triangles or the like in contact with the lines. Further, the lines indicating the movement amounts do not need to be straight lines. For example, the movement amounts may each be expressed by a semicircle, an arc or the like with adjacent foot landing positions as its respective ends. Further, the lines, which extend, may be omitted, and, for example, only the foot landing positions of the user with or without the animation of the person figure representing the user may be displayed.

Further, in the above embodiment, the user needs to start and end the activity measurement function, but this is not a limitation. The activity measurement (activity measurement function) may be automatically started when exercise of a predetermined intensity is detected, and in this case, if the exercise of the predetermined intensity is not continued for a time equal to or longer than a lower-limit reference value, data obtained by the activity measurement may be deleted. On the other hand, the activity measurement may be automatically ended if exercise of a predetermined intensity is not detected for a time equal to or longer than a predetermined time. Before the activity measurement is automatically ended, some sort of informing process may be performed to inform the user of that.

Further, in the above embodiment, two cases are described mainly, in one of which the electronic device 100 obtains measured data with its measurer 15, and in the other of which the electronic device 100 receives/obtains measured data from an external device, but these cases may be combined as appropriate. For example, the electronic device 100 may receive radio waves from positioning satellites by itself, and obtain, from an external device, measured data by an acceleration sensor and a heart rate sensor.

Further, in the above embodiment, the walking state of the user is displayed, but the running state of the user may also be displayed in the same/similar manner.

Further, in the above embodiment, the storage 12 including a nonvolatile memory, such as a flash memory, is used as a computer-readable storage medium storing the running/walking management program 121. However, the computer-readable storage medium is not limited thereto but another nonvolatile memory, such as an MRAM, an HDD (Hard Disk Drive), or a portable storage medium, such as a CD-ROM or a DVD. Further, as a medium to provide data of the program(s) of the present disclosure via a communication line, a carrier wave may be used.

Besides, detailed configurations/components of the electronic device 100, contents and procedures of the processes, and so forth described in the above embodiment can be appropriately modified without departing from the scope of the present disclosure.

Although one or more embodiments of the present disclosure have been described above, the scope of the present disclosure is not limited to the above embodiments, but includes the scope of claims and the scope of their equivalents.

What is claimed is:

1. A display control method for a display control device including a processor and a storage, the display control method being performed by the processor executing a program stored in the storage, the display control method comprising:
   (i) generating first display data for a display to display user marks at intervals, each user mark corresponding to a user's step length of a user obtained based on measured data on running or walking of the user such that the user marks are added one by one as a time elapses from a timing, each of the user marks representing a foot of the user landing when taking one step;
   (ii) generating second display data for the display to display reference marks at intervals, each of the reference marks corresponding to a predetermined reference step length such that the reference marks are added one by one as the time elapses, each of the reference marks representing a reference foot landing when taking one step;
   (iii) causing the display to display the first display data;
   (iv) causing the display to display the second display data;
   (v) causing the display to display a user's movement amount based on a user's moving speed from the timing, the user's moving speed being obtained based on the measured data, using a length of a first line that extends in a direction as the time elapses;

(vi) causing the display to display a reference movement amount based on a predetermined reference moving speed from the timing using a length of a second line that extends in the direction as the time elapses; and (vii) causing the display to display the user marks and the reference marks so as to correspond to the first line and the second line, respectively.

2. The display control method according to claim 1, wherein (vii) includes causing the display to display the user marks on the first line and the reference marks on the second line.

3. The display control method according to claim 1, further comprising:
(viii) causing the display to display the first line and the second line parallel to one another with a same position in the direction, in which the first line and the second line extend as the time elapses, as a starting point of the first line and the second line; and
(ix) causing the display to display, parallel to the first line and the second line, an animation representing the user who moves by running or walking with the user's step length and an animation representing a reference person who moves by running or walking with the reference step length.

4. The display control method according to claim 3, wherein (ix) includes causing the display to display, on a same line, the animation representing the user at the user's moving speed with the user's step length and the animation representing the reference person at the reference moving speed with the reference step length.

5. The display control method according to claim 1, wherein the first line and the second line are caused to be displayed as straight lines that are parallel to each other.

6. The display control method according to claim 1, wherein the first line is caused to be displayed to extend in the direction at a first display speed that is based on the user's moving speed; and
wherein the second line is caused to be displayed to extend in the direction at a second display speed that is based on the reference moving speed.

7. A display control device comprising a processor that:
obtains measured data on running or walking of a user,
generates first display data for a display to display user marks at intervals, each user mark corresponding to a user's step length of the user obtained based on the measured data such that the user marks are added one by one as a time elapses from a timing, each of the user marks representing a foot of the user landing when taking one step, and
generates second display data for the display to display reference marks at intervals, each of the reference marks corresponding to a predetermined reference step length such that the reference marks are added one by one as the time elapses, each of the reference marks representing a reference foot landing when taking one step,
causes the display to display the first display data,
causes the display to display the second display data,
causes the display to display a user's movement amount based on a user's moving speed from the timing, the user's moving speed being obtained based on the measured data, using a length of a first line that extends in a direction as the time elapses,
causes the display to display a reference movement amount based on a predetermined reference moving speed from the timing using a length of a second line that extends in the direction as the time elapses, and
causes the display to display the user marks and the reference marks so as to correspond to the first line and the second line, respectively.

8. The display control device according to claim 7, wherein the processor causes the display to display the user marks on the first line and the reference marks on the second line.

9. The display control device according to claim 7, wherein the processor:
causes the display to display the first line and the second line parallel to one another with a same position in the direction, in which the first line and the second line extend as the time elapses, as a starting point of the first line and the second line, and
causes the display to display, parallel to the first line and the second line, an animation representing the user who moves by running or walking with the user's step length and an animation representing a reference person who moves by running or walking with the reference step length.

10. The display control device according to claim 9, wherein the processor causes the display to display, on a same line, the animation representing the user at the user's moving speed with the user's step length and the animation representing the reference person at the reference moving speed with the reference step length.

11. The display control device according to claim 7, wherein the processor causes the display to display the first line and the second line as straight lines that are parallel to each other.

12. The display control device according to claim 7, wherein the processor:
causes the display to display the first line to extend in the direction at a first display speed that is based on the user's moving speed; and
causes the display to display the second line to extend in the direction at a second display speed that is based on the reference moving speed.

13. A non-transitory computer-readable storage medium storing a program that is executable by a computer to perform operations comprising:
generating first display data for a display to display user marks at intervals, each user mark corresponding to a user's step length of a user obtained based on measured data on running or walking of the user such that the user marks are added one by one as a time elapses from a timing, each of the user marks representing a foot of the user landing when taking one step; and
generating second display data for the display to display reference marks at intervals, each of the reference marks corresponding to a predetermined reference step length such that the reference marks are added one by one as the time elapses, each of the reference marks representing a reference foot by landing when taking one step;
causing the display to display the first display data;
causing the display to display the second display data;
causing the display to display a user's movement amount based on a user's moving speed from the timing, the user's moving speed being obtained based on the measured data, using a length of a first line that extends in a direction as the time elapses;
causing the display to display a reference movement amount based on a predetermined reference moving speed from the timing using a length of a second line that extends in the direction as the time elapses; and causing the display to display the user marks and the reference marks so as to correspond to the first line and the second line, respectively.

14. The non-transitory computer-readable storage medium according to claim 13, wherein the first line and the second line are caused to be displayed as straight lines that are parallel to each other.

15. The non-transitory computer-readable storage medium according to claim 13, wherein the first line is caused to be displayed to extend in the direction at a first display speed that is based on the user's moving speed; and
wherein the second line is caused to be displayed to extend in the direction at a second display speed that is based on the reference moving speed.

* * * * *

UNITED STATES PATENT AND TRADEMARK OFFICE
CERTIFICATE OF CORRECTION

PATENT NO. : 12,426,806 B2
APPLICATION NO. : 17/949810
DATED : September 30, 2025
INVENTOR(S) : Shosaku Suzuki et al.

Page 1 of 1

It is certified that error appears in the above-identified patent and that said Letters Patent is hereby corrected as shown below:

In the Claims

Column 18, Line 55 (counted Line 54), after "foot" delete "by".

Signed and Sealed this
Sixteenth Day of December, 2025

John A. Squires
*Director of the United States Patent and Trademark Office*